United States Patent [19]

Schreiber et al.

[11] Patent Number: 4,490,562
[45] Date of Patent: Dec. 25, 1984

[54] PROCESS FOR THE PREPARATION OF A VERY PURE COMMERCIAL FORM OF 4,2',4'-TRICHLORO-2-HYDROXYDIPHENYL ETHER

[75] Inventors: Werner Schreiber, Basel; Michael Märky, Allschwil, both of Switzerland

[73] Assignee: Ciba-Geigy Corporation, Ardsley, N.Y.

[21] Appl. No.: 462,258

[22] Filed: Jan. 31, 1983

[30] Foreign Application Priority Data

Feb. 11, 1982 [CH] Switzerland .............................. 853/82

[51] Int. Cl.³ ...................... C07C 41/38; C07C 41/40; C07C 41/42
[52] U.S. Cl. .................................................... 568/637
[58] Field of Search ......................................... 568/637

[56] References Cited

U.S. PATENT DOCUMENTS 3,506,720  4/1970  Model et al. ......................... 568/637
3,629,477  12/1971 Model et al. .
3,642,872  2/1972  Model et al. .
3,784,698  1/1974  Model et al. .
3,800,048  3/1974  Model et al. .
3,904,696  9/1975  Model et al. .
4,355,189  10/1982 Volkwein .

Primary Examiner—Bernard Helfin
Attorney, Agent, or Firm—Edward McC. Roberts

[57] ABSTRACT

A very pure, dust-free commercial form of 4,2',4'-trichloro-2-hydroxydiphenyl ether with little odor is prepared by diazotizing 4,2'4'-trichloro-2-aminodiphenyl ether, boiling the diazonium salt and purifying the reaction product. The pure, dust-free and odor-free commercial form is obtained by separating off the acid aqueous phase of the reaction mixture, rendering the mixture containing 4,2'4'-trichloro-2-hydroxydiphenyl ether and 2,4,8-trichlorodibenzofuran alkaline, extracting it several times with an inert water-immiscible solvent, either after removal of the organic solvent by steam distillation and precipitation of the by-product 2,4,8-trichlorodibenzofuran or directly, and then adjusting the pH to 3 to 10; subsequently, the highly volatile constituents are removed from the 4,2',4'-trichloro-2-hydroxydiphenyl ether melt which has separated out, the melt is subjected to molecular distillation and the distilled melt is introduced into an aqueous dispersion of crystalline 4,2',4'-trichloro-2-hydroxydiphenyl ether, this dispersion simultaneously being subjected to wet grinding. Filtration and drying gives a granular-like ready-to-use commercial form.

25 Claims, No Drawings

PROCESS FOR THE PREPARATION OF A VERY PURE COMMERCIAL FORM OF 4,2',4'-TRICHLORO-2-HYDROXYDIPHENYL ETHER

The present invention relates to a process for the preparation of a very pure, dust-free granular commercial form of 4,2',4'-trichloro-2-hydroxydiphenyl ether with little odour.

Halogenated 2-hydroxydiphenyl ethers are known to be good antimicrobial active ingredients, cf., for example, U.S. Pat. Nos. 3,904,696, 3,629,477 and 3,800,048 and Swiss Pat. No. 432,119. Because of its outstanding properties as a bactericidal and fungicidal active ingredient, 4,2',4'-trichloro-2-hydroxydiphenyl ether has already been commercially available for a long time. It is used as disinfecting active ingredient in, for example, soaps, detergents, cosmetics and other household articles. On the basis of this use, very high purity requirements are imposed on the active ingredient. It is therefore particularly important that 4,2',4'-trichloro-2-hydroxydiphenyl ether is prepared in an extremely pure form, i.e. containing as few by-products as possible, and that this purity is achieved by an exceptionally rational and industrially optimum process.

Possible preparation processes for the compound mentioned are described in the above patents. The only preparation process which has hitherto been used on a large industrial scale is that described in principle in German Auslegeschrift No. 1,216,882 (cf., in particular, Example 1). This process is carried out as follows: 4,2',4'-trichloro-2-aminodiphenyl ether is diazotised in concentrated sulfuric acid and the resulting diazonium salt is boiled in about 50–80% sulfuric acid, if necessary after addition of o-dichlorobenzene. For working up, the resulting mixture of 4,2',4'-trichloro-2-hydroxydiphenyl ether and 2,4,8-trichlorodibenzofuran (by-product) is rendered strongly alkaline and, if necessary, any organic solvent present is distilled off with steam. The by-product is filtered off and the 4,2',4'-trichloro-2-hydroxydiphenyl ether is precipitated in the filtrate by adjusting the pH to a value somewhat above 9. For further purification, the product is distilled in vacuo and is then recrystallised from petroleum ether.

Although the chemical preparation process via diazotisation and boiling produces a large amount of the above by-product, it seems to be the only practical process in industry. The problem is chiefly that of carrying out the working up in a manner such that as little product as possible has to be lost, the impurities are reduced to the required degree, the working up is technically as simple as possible and, in particular, is acceptable from the point of view of operational safety, and the resulting product is obtained in a commercially usable form.

The above process which has hitherto been carried out, and especially the working up and purification, has some disadvantages:

(1) In order to fulfil the required purity criteria, a recrystallisation step (from petroleum ether), which is particularly expensive on a large industrial scale, must be included after the vacuum distillation of the end product. This recrystallisation is a substantial safety risk because of the static charge of the product.

(2) Undesirable reactions occur during the vacuum distillation, during which the product must be heated to a relatively high temperature, and these reactions in turn lead to undesirable by-products and decrease the final yield.

(3) In spite of the expensive purification operations mentioned, the resulting product still contains some by-products, elimination of which would be desirable.

(4) The product is obtained as a powder, which is not an ideal commercial form since it tends to dust and agglomerate.

(5) The product has a characteristic odour which is undesirable.

The object of the present invention was to design the working up and purification in the above base process such that the disadvantages described do not occur or are diminished and in addition other technical advantages result. Surprisingly, this object was achieved by a combination of particular separation and purification steps. The advantages achieved by the process according to the invention are, inter alia:

(1) A particularly pure end product which completely fulfils the required purity criteria is obtained.

(2) A technically doubtful recrystallisation is no longer necessary.

(3) The final yield can be substantially increased.

(4) The product is obtained as dust-free, pourable and hence easily meterable granules which have little odour and are an excellent commercial form.

The process for the preparation of a very pure, dust-free granular commercial form of 4,2',4'-trichloro-2-hydroxydiphenyl ether with little odour by diazotisation of 4,2',4'-trichloro-2-aminodiphenyl ether, boiling of the resulting diazonium salt and working up of the reaction mixture containing the reaction products 4,2',4'-trichloro-2-hydroxydiphenyl ether and 2,4,8-trichlorodibenzofuran comprises, for the working up and purification, (a) rendering the mixture which is obtained after boiling the diazonium salt and separating off the aqueous acid phase and which contains 4,2',4'-trichloro-2-hydroxydiphenyl ether and 2,4,8-trichlorodibenzofuran strongly alkaline and ($\alpha$) subjecting it to steam distillation to remove the organic solvent, if such a solvent was present in the reaction mixture, filtering off the 2,4,8-trichlorodibenzofuran precipitated and extracting the filtrate several times with an inert water-immiscible organic solvent, or ($\beta$) if only little or no solvent was present in the reaction mixture, extracting the alkaline mixture directly several times with an inert water-immiscible organic solvent, (b) adjusting the pH value of the strongly alkaline aqueous phase to 3 to 10 with acid and separating off the 4,2',4'-trichloro-2-hydroxydiphenyl ether obtained as a melt, (c) removing highly volatile constituents from this melt, if desired after addition of a diluent of low volatility, and then subjecting the said melt to molecular distillation, (d) introducing the distilled melt into an aqueous dispersion of crystalline 4,2',4'-trichloro-2-hydroxydiphenyl ether, this dispersion simultaneously being subjected to wet grinding, and (e) filtering off and drying the resulting granular product.

The diazotisation of the 4,2',4'-trichloro-2-aminodiphenyl ether and the boiling of the diazonium salt to give the corresponding hydroxy compound can be carried out by conventional processes which are known from the literature, for example as described in the patents quoted above. 4,2',4'-Trichloro-2-aminodiphenyl ether can advantageously be diazotised with nitrosylsulfuric acid in sulfuric acid. The diazonium salt can then be boiled, for example, at temperatures above 100° C., if desired after addition of a high-boiling solvent (for example o-dichlorobenzene), cf., for example, Example 1 of German Auslegeschrift No. 1,216,882.

The resulting reaction mixture is strongly acid. The acid aqueous phase is first separated off from the mixture containing 4,2',4'-trichloro-2-hydroxydiphenyl ether and 2,4,8-trichlorodibenzofuran. If an organic solvent had been added for the boiling step, this mixture may be dissolved in this solvent. In the first step according to the invention (step (a)), this mixture is first rendered strongly alkaline, and in a first embodiment is subjected to steam distillation, in order to remove any solvent present from the boiling of the diazonium salt (for example o-dichlorobenzene). The 2,4,8-trichlorodibenzofuran precipitates in the residue from the steam distillation and is filtered off. The filtrate is extracted several times, preferably at least 3 times, for example 3 to 10 times and especially 3 to 7 times, with an inert water-immiscible organic solvent. If only very little or no organic solvent is present in the reaction mixture after boiling of the diazonium salt and hence also in the mixture containing the crude products, steam distillation is of course unnecessary. In this case, after the mixture has been rendered strongly alkaline (crude product mixture in the form of a melt), the 2,4,8-trichlorodibenzofuran precipitated is filtered off directly and the filtrate is extracted as described above.

In a second embodiment, if only a little or no solvent was present in the reaction mixture after the boiling, the aqueous acid phase is likewise separated off from the crude product mixture (melt) which contains 4,2',4'-trichloro-2-hydroxydiphenyl ether and 2,4,8-trichlorodibenzofuran and possibly also a little solvent, and the crude product mixture is rendered strongly alkaline. The alkaline melt (crude product mixture) is then extracted several times with an inert water-immiscible organic solvent. The by-product 2,4,8-trichlorodibenzofuran is in this way substantially removed, together with other impurities. The extraction is preferably carried out at least 3 times, for example 3 to 10 times and especially 3 to 7 times.

The solvent extracts obtained are preferably washed with sodium hydroxide solution in order to recover any end product which has entered the solvent phase. The alkaline wash solution is then added to a new batch of alkaline crude product solution which has not yet been extracted.

The above removal of the melt containing 4,2',4'-trichloro-2-hydroxydiphenyl ether and 2,4,8-trichlorodibenzofuran or of the organic phase containing this melt from the acid aqueous reaction medium is preferably carried out at elevated temperature, for example at about 100° to 120° C.

As has already been described, the crude product mixture according to stage (a) obtained after having separated off the aqueous acid phase is rendered strongly alkaline, and in particular in a manner such that 4,2',4'-trichloro-2-hydroxydiphenyl ether passes into solution as a salt. The pH value is preferably adjusted to $\geq 11$. This pH value can be established, for example, with an aqueous solution of an alkali metal hydroxide, in particular sodium hydroxide.

The solvent used according to step (a) for the extraction must be inert towards the products contained in the mixture, is water-immiscible, and should not be attacked by the alkaline medium. Examples of such solvents include aromatic or aliphatic hydrocarbons, halogenated aromatic or aliphatic hydrocarbons, water-immiscible ethers, ketones and the like, but especially aromatic or aliphatic hydrocarbons or halogenated aromatic or aliphatic hydrocarbons. Aromatic hydrocarbons or halogenated (for example chlorinated) aromatic or aliphatic hydrocarbons are preferred. Examples of such solvents are methylene chloride, chloroform, carbon tetrachloride, ethylene chloride, tetrachloroethane, 1,2-dichloroethane, 1,1,1-trichloroethane, perchloroethylene, trichloroethylene, 1,1,2-trichloro-trifluoroethane, dichlorobenzenes, such as 1,2-dichlorobenzene, trichlorobenzenes, toluene and xylenes. Dichlorobenzenes, for example 1,2-dichlorobenzene, and toluene or xylene (for example a xylene isomer mixture) are particularly advantageously used.

The extractions according to step (a) are preferably carried out in a temperature range between room temperature and about 95° C. Temperatures between 45° and 85° C. have proved particularly advantageous. The extraction temperature largely depends, of course, on the solvent used.

The purified, strongly alkaline aqueous phase obtained after the extraction is now adjusted to a pH value of 3 to 10, according to step (b) with any acid in order to precipitate the 4,2',4'-trichloro-2-hydroxydiphenyl ether. The product obtained as a melt is separated off. The precipitation is preferably carried out at a pH value of 8-10, in particular 9-9.5.

Highly volatile impurities which are still present, such as solvent residues and the like, are first removed from the product melt obtained according to step (b). This can be effected in a conventional distillation apparatus, preferably in a falling film evaporator. Alternatively, the highly volatile constituents can also be removed directly in the molecular distillation apparatus in an additional distillation stage.

Before the distillation, a small amount of a diluent of low volatility, for example a polyethylene glycol, is preferably added to the melt in order thus to maintain a liquid distillation residue. Cleaning of the distillation apparatus is thereby substantially facilitated.

After the highly volatile constituents have been removed, the product melt is subjected to molecular distillation according to step (c). Generally known molecular distillation apparatuses (molecular evaporators), such as are described in the literature (cf., for example, Ullmanns Encyklopädie der technischen Chemie [Ullmann's Encyclopedia of Industrial Chemistry], 4th Edition, Volume 2, pages 657 and 658) are used for this purpose.

For the purification of 4,2',4'-trichloro-2-hydroxydiphenyl ether, molecular distillation has the particular advantage that very high temperatures do not have to be used during the distillation and that the product is exposed to elevated temperatures for only a very short time (in molecular distillation, the distillation path is of the same order of size as the mean free path of the molecules). Formation of decomposition and condensation products (for example dibenzodioxines), such as occur in an undesirable manner in conventional distillation, is in this way substantially avoided. For optimum utilisation of the advantages mentioned, the distillation is preferably carried out under very low pressures, pressures of the order of about $10^{-3}$ mbar preferably being applied.

Although one distillation step would be sufficient to achieve the required purity criteria, the product melt is preferably distilled twice. An even purer end product is then obtained, and the distillate which may still have a slight yellowish colouration after the first distillation becomes virtually colourless.

Because of the relatively low melting point of 4,2',4'-trichloro-2-hydroxydiphenyl ether (55°–60° C.), crystallisation of the melt presented certain difficulties in the processes hitherto used. In addition, the resulting crystalline powder was not the optimum commercial form, since it was not dust-free and also tended to form lumps. In step (d) according to the invention, the distillate obtained according to step (c) is simultaneously crystallised and processed to a granular commercial form. For this purpose, the distillate is introduced into an aqueous dispersion of crystalline 4,2',4'-trichloro-2-hydroxydiphenyl ether, the dispersion simultaneously being subjected to wet grinding.

The crystallisation and granulation step (d) is preferably carried out at temperatures from 10° to 50° C., in particular from 30°–45° C. The dispersion into which the distilled product is introduced may contain very small amounts of crystalline 4,2',4'-trichloro-2-hydroxydiphenyl ether. In the case of very small amounts, the product distillate is advantageously added slowly, in order to achieve crystallisation. The aqueous dispersion preferably contains at least about 0.01% by weight, in particular at least about 0.1% by weight, for example at least about 0.5% by weight, of crystalline 4,2',4'-trichloro-2-hydroxydiphenyl ether at the start of metering in of the product distillate. The proportion of crystallised product in the dispersion increases as a result of addition of the product to be crystallised, and in practice increases as long as the dispersion is still easily stirrable. For example, when the content of crystallised product in the dispersion is about 30–40%, no further product melt is fed in and the crystalline granular 4,2',4'-trichloro-2-hydroxydiphenyl ether is filtered off.

Since the dispersion is subjected to wet grinding during the crystallisation step, the latter is advantageously carried out in a conventional wet grinding unit. A large number of appropriate units are known from the literature and are commercially available. The wet grinding can be carried out in, for example, a conventional ball mill; however, it is preferably carried out in a colloid mill, in particular a colloid mill based on the rotor-stator principle or in a gear-type colloid mill.

The granules obtained according to step (d) are filtered and are dried in a conventional manner. The resulting dry, pure-white granules are free-flowing, do not tend to agglomerate and are virtually odourless.

The examples which follow serve to illustrate the process according to the invention in more detail. Parts and percentages, both in the examples and in the remainder of the description and the claims, are by weight, unless indicated otherwise.

EXAMPLE 1

92 g of nitrosylsulfuric acid (100%) are dissolved in 720 g of concentrated sulfuric acid, and 200 g of 4,2',4'-trichloro-2-aminodiphenyl ether are introduced at 50° to 55° C. in the course of 2 hours, while stirring thoroughly. The mixture is stirred for a further 3 hours at room temperature. 210 ml of water are then allowed to run in, while the mixture is cooled with ice-water, the temperature rising to 70° C. After 370 ml of o-dichlorobenzene have been added, the mixture is boiled in an oil bath at 200° C. until the diazo compound can no longer be detected. The upper organic layer is then separated off while still hot, 460 ml of water are added and the pH value is then adjusted to $\geq 11$ with 30% sodium hydroxide solution. Thereafter, the mixture is subjected to steam distillation in order to remove the o-dichlorobenzene. The 2,4,8-trichlorodibenzofuran which has precipitated in the aqueous residue is filtered off and washed.

The combined filtrates are introduced into a flask, 50 ml of 1,2-dichlorobenzene are added and the mixture is heated to 50° C. The mixture is stirred vigorously for 10 minutes. When the stirrer has been switched off, the layers separate over a period of 20–30 minutes. The lower 1,2-dichlorobenzene phase is separated off, and another 50 ml of 1,2-dichlorobenzene are added to the aqueous layer, which is then stirred at 50° C. This extraction operation is repeated four times. The aqueous phase is then adjusted to pH 9–9.5 with 65% sulfuric acid. The resulting emulsion is stirred for another 30 minutes, the pH value is checked again, the stirrer is switched off and the oily melt of 4,2',4'-trichloro-2-hydroxydiphenyl ether which deposits is separated off.

3 g of polyethylene glycol 600 are added to the melt which has been separated off. The highly volatile constituents still present are then removed in a falling film evaporator at 100° C. and under 15–30 mbar. The degassed crude product is now distilled in a molecular evaporator under a pressure of about $10^{-3}$ mbar (jacket temperature about 140°–160° C.), the impurities of low volatility remaining together with the polyethylene glycol. The resulting distillate which is already pure but still somewhat yellowish is distilled again (jacket temperature 120°–130° C.). The residue of this purification stage is added again to the subsequent distillation stage of further 4,2',4'-trichloro-2-hydroxydiphenyl ether.

The distilled melt is now introduced into a dropping funnel, which can be heated, and metered into a dispersion of 5 g of crystalline 4,2',4'-trichloro-2-hydroxydiphenyl ether in 300 ml of deionised water at a temperature of 35°–45° C. During this, the dispersion is stirred intensively in a colloid mill based on the rotor-stator principle (for example Ultra-Turrax ®, Polytron ®). The particle size of the granules finally obtained can be determined by the stirring speed: finer granules are obtained with higher-speed stirring and coarser granules are obtained with slower stirring. The resulting granules are filtered off and dried. They form hardly any dust, are virtually odourless and do not form lumps even on prolonged storage.

According to analysis by gas chromatography, the product thus obtained contains more than 99.5% of 4,2',4'-trichloro-2-hydroxydiphenyl ether, less than 1 ppm of 2,4,8-trichlorodibenzofuran and less than 2 ppm of 2,8-dichloro-p-dibenzodioxine. It also no longer contains troublesome odour components.

The procedure described above is repeated, except that 1,2-dichloroethane, 1,1,2,2-tetrachloroethylene, carbon tetrachloride, 1,1,2-trichloro-trifluoroethane, toluene, o-xylene, m-xylene, p-xylene or a xylene isomer mixture is used instead of 1,2-dichlorobenzene as the solvent in the extraction step, likewise affording a pure end product as defined above.

EXAMPLE 2

92 g of nitrosylsulfuric acid (100%) are dissolved in 720 g of concentrated sulfuric acid, and 200 g of 4,2',4'-trichloro-2-aminodiphenyl ether are introduced at 40° to 45° C. in the course of 2 hours, while stirring thoroughly. The mixture is stirred for a further 3 hours at room temperature. 210 ml of water are then allowed to run in, while cooling with ice-water, the temperature rising to 70° C. Thereafter, the mixture is boiled in an oil bath at 200° C. until the diazo compound can no longer be detected. The two-phase reaction mixture is then brought to a temperature of 120° C. and the melt containing 4,2',4'-trichloro-2-hydroxydiphenyl ether and 2,4,8-trichlorodibenzofuran is separated off from the aqueous reaction medium containing sulfuric acid.

83 ml of 30% sodium hydroxide solution, 720 ml of water and 230 ml of toluene are introduced into a double-wall flask with a ground-glass joint, a bottom discharge, an anchor stirrer, a thermometer, a pH meter and a reflux condenser, and the mixture is warmed to 80°–83° C. The product melt which has been separated off as described above is added, while stirring vigorously. The pH value of the two-phase mixture is monitored and, if necessary, adjusted to the intended value of ≧11 with sodium hydroxide solution. The mixture is stirred for 15 minutes, the pH value is checked again and the stirrer is then switched off and, after 15 minutes, the aqueous phase is separated off into a double-wall flask with a ground-glass joint and cooled to 50°–60° C. A further 50 ml of toluene are added to the aqueous alkaline solution and the mixture is stirred thoroughly for 10 minutes. 20–30 minutes after the stirrer has been switched off, the lower aqueous phase is separated off. This extraction process is repeated a total of 5 times. The toluene phases obtained are combined and are extracted with 3–5 100 ml portions of 1N NaOH at 50° C. This aqueous extract is added to a new batch of alkaline crude product solution which has not yet been extracted.

The extracted aqueous phase is now adjusted to a pH value of 9.2–9.5 with 65% sulfuric acid, and the temperature is kept below 60° C. The resulting emulsion is stirred at 50° to 55° C. for 30 minutes and the pH value is checked again and, if necessary, corrected. The stirrer is then switched off and the oily melt of 4,2',4'-trichloro-2-hydroxydiphenyl ether which deposits is separated off after about 30 minutes.

3 g of polyethylene glycol 600 are added to the melt which has been separated off. The highly volatile constituents which are still present are then removed in a falling film evaporator at 100° C. and under 15–30 mbar. The degassed crude product is now distilled in a molecular evaporator under a pressure of about $10^{-3}$ mbar (jacket temperature about 140°–160° C.), the impurities of low volatility remaining together with the polyethylene glycol. The resulting distillate, which is already pure but still somewhat yellowish, is distilled again (jacket temperature 120°–130° C.). The residue from this purification stage is added again to the subsequent distillation stage of further crude 4,2',4'-trichloro-2-hydroxydiphenyl ether.

The distilled melt is now introduced into a dropping funnel which can be heated, and metered into a dispersion of 5 g of crystalline 4,2',4'-trichloro-2-hydroxydiphenyl ether in 300 ml of deionised water at a temperature of 35°–45° C. During this, the dispersion is stirred intensively in a colloid mill based on the rotor-stator principle (for example Ultra-Turax ®, Polytron ®). The particle size of the granules finally obtained can be determined by the stirring speed: finer granules are obtained with higher-speed stirring and coarser granules are obtained with slower stirring. The resulting granules are filtered off and dried. They form hardly any dust, are virtually odourless and do not form lumps even on prolonged storage.

According to analysis by gas chromatography, the product thus obtained contains more than 99.5% of 4,2',4'-trichloro-2-hydroxydiphenyl ether, less than 1 ppm of 2,4,8-trichlorodibenzofuran and less than 2 ppm of 2,8-dichloro-p-dibenzodioxine. It also no longer contains troublesome odour components.

The procedure described above is repeated, except that other aromatic hydrocarbons, for example xylene, are used instead of toluene as the solvent for extraction of the melt, likewise affording a pure end product as defined above.

The extraction can, however, also be carried out with, for example, 1,2-dichlorobenzene, 1,1,2,2-tetrachloroethane, tetrachloroethylene, chloroform or 1,1,2-trichlorotrifluoroethane.

What is claimed is:

1. In a process for the preparation of 4,2',4'-trichloro-2-hydroxydiphenyl ether by diazotizing 4,2',4'-trichloro-2-amino-diphenyl ether and boiling the diazonium salt to produce the product contaminated with 2,4,8-trichlorodibenzofuran, isolating the contaminated product and purifying the product, the improvement which comprises the steps of
   (1) separating the reaction mixture at the end of the reaction into its organic and aqueous phases,
   (2) adjusting the pH of the organic phase to pH 11 or more with aqueous alkali to give an aqueous solution of the product,
   (3) extracting the alkaline aqueous solution with an inert, water-immiscible, organic liquid which is a solvent for 2,4,8-trichlorodibenzofuran,
   (4) discarding the organic liquid extract,
   (5) adjusting the pH of the alkaline aqueous solution following step 3 by addition of aqueous acid to give a pH in the range of 3 to 10 to cause separation of the product,
   (6) subsequently subjecting the product to molecular distillation, and
   (7) introducing the distillate from step 6 into an aqueous dispersion of pure crystalline product while wet grinding said dispersion to give the pure product in granular form.

2. The improvement of claim 1, comprising the additional step of removing any volatile reaction solvent from the organic phase by steam distillation, following step 2 and prior to step 3.

3. The improvement of claim 1, comprising the additional step of removing the 2,4-8-trichlorodibenzofuran by filtration from the aqueous solution, following step 2 and prior to step 3.

4. The improvement of claim 2, comprising the additional step of removing the 2,4-8-trichlorodibenzofuran by filtration, after the steam distillation and prior to step 3.

5. The improvement of claim 1, comprising the repetition of steps 3 and 4 several times before proceeding to step 5.

6. The improvement of claim 1, comprising the additional step of extracting the organic liquid extract of step 3 with aqueous alkali at pH 11 or more before discarding the organic liquid extract in step 4 and adding the aqueous alkali extract which contains product to a new batch prior to step 3.

7. The improvement of claim 1, comprising the additional step of removing any highly volatile contaminants from the product by evaporation between steps 5 and 6.

8. The improvement of claim 1, wherein the organic liquid of step 3 is an aliphatic or aromatic hydrocarbon or a halogenated aliphatic or aromatic hydrocarbon.

9. The improvement of claim 8 wherein the organic liquid is an aromatic hydrocarbon or a halogenated aliphatic or aromatic hydrocarbon.

10. The improvement of claim 9, wherein the organic liquid is methylene chloride, chloroform, carbon tetrachloride, ethylene chloride, tetrachloroethane, 1,2-dichloroethane, 1,1,1-trichloroethane, perchloroethylene, trichloroethylene, 1,1,2-trichloro-trifluoroethane, dichlorobenzene, trichlorobenzene, toluene or xylene.

11. The improvement of claim 10, wherein the organic liquid is 1,2-dichlorobenzene, toluene or xylene.

12. The improvement of claim 5, wherein steps 3 and 4 are repeated 3 to 10 times.

13. The improvement of claim 1, wherein step 3 is carried out at a temperature in the range of room temperature to 95° C.

14. The improvement of claim 13, wherein step 3 is carried out at a temperature in the range of 45°–85° C.

15. The improvement of claim 1, wherein, in step 5, the adjusted pH value is in the range of 8–10.

16. The improvement of claim 7, wherein polyethylene glycol is added to the product before the highly volatile contaminants are removed by evaporation.

17. The improvement of claim 7, wherein the evaporation of the highly volatile contaminants is carried out in an additional distillation stage in the molecular distillation apparatus of step 6.

18. The improvement of claim 7, wherein the evaporation of highly volatile contaminants is carried out in a falling film evaporator.

19. The improvement of claim 1, wherein the molecular distillation of step 6 is carried out at about $10^{-3}$ mbar pressure.

20. The improvement of claim 1, wherein step 6 is repeated before proceeding to step 7.

21. The improvement of claim 1, wherein the distillate is mixed as a melt with the aqueous dispersion of pure crystalline product at a temperature in the range of 10°–50° C.

22. The improvement of claim 1, wherein the aqueous dispersion of step 7 contains at least 0.1% of pure crystalline product before mixing with the distillate.

23. The improvement of claim 1, wherein the wet grinding of step 7 is carried out in a colloid mill based on the rotor-stator principle.

24. The improvement of claim 15, wherein the adjusted pH value is in the range of 9–9.5.

25. The improvement of claim 22, wherein the aqueous dispersion contains at least 0.5% of pure crystalline product before mixing with the distillate.

* * * * *